US010622099B2

United States Patent
Cox et al.

(10) Patent No.: US 10,622,099 B2
(45) Date of Patent: Apr. 14, 2020

(54) SYSTEMS AND METHODS FOR SUPPORTING HOSPITAL DISCHARGE DECISION MAKING

(71) Applicants: Georgia State University Research Foundation, Inc., Atlanta, GA (US); Emory University, Atlanta, GA (US)

(72) Inventors: James C. Cox, Marietta, GA (US); Vjollca Sadiraj, Marietta, GA (US); Kurt E. Schnier, Smyrna, GA (US); John F. Sweeney, Snellville, GA (US)

(73) Assignees: Georgia State University Research Foundation, Inc., Atlanta, GA (US); Emory University, Atlanta, GA (US)

( * ) Notice: Subject to any disclaimer, the term of this patent is extended or adjusted under 35 U.S.C. 154(b) by 1014 days.

(21) Appl. No.: 14/888,620

(22) PCT Filed: May 2, 2014

(86) PCT No.: PCT/US2014/036609
§ 371 (c)(1),
(2) Date: Nov. 2, 2015

(87) PCT Pub. No.: WO2014/179712
PCT Pub. Date: Nov. 6, 2014

(65) Prior Publication Data
US 2016/0085931 A1    Mar. 24, 2016

Related U.S. Application Data

(60) Provisional application No. 61/819,130, filed on May 3, 2013.

(51) Int. Cl.
*G16H 10/60*    (2018.01)
*G16H 50/20*    (2018.01)
(Continued)

(52) U.S. Cl.
CPC ........... *G16H 10/60* (2018.01); *G06Q 10/103* (2013.01); *G06Q 50/22* (2013.01); *G06Q 50/24* (2013.01);
(Continued)

(58) Field of Classification Search
CPC ...... G06F 19/345; G16H 15/00; G16H 50/20; G16H 40/20; G16H 10/60; G16H 10/00;
(Continued)

(56) References Cited

U.S. PATENT DOCUMENTS

| 8,095,380 B2 | 1/2012 | Wennberg |
| 8,392,216 B2 | 3/2013 | Crockett |

(Continued)

FOREIGN PATENT DOCUMENTS

| WO | 2012104803 | 8/2012 |
| WO | 2012176104 | 12/2012 |

(Continued)

OTHER PUBLICATIONS

International Search Report for PCT/US2014/036609 dated Sep. 29, 2014.
(Continued)

*Primary Examiner* — Eliza A Lam
(74) *Attorney, Agent, or Firm* — Thomas | Horstemeyer, LLP

(57) ABSTRACT

In one embodiment, a system and method for assisting a physician with a hospital discharge decision pertain to collecting patient data from a patient under consideration who is staying at a hospital, estimating a mathematical probability of the patient under consideration being readmitted to the hospital within a predetermined amount of time if the patient under consideration were discharged on that day, wherein the mathematical probability estimate is based upon the collected patient data and patient data collected
(Continued)

from a population of former hospital patients who had previously been discharged and whose readmission status is known, and providing information to the physician that assists the physician in deciding whether or not to discharge the patient under consideration, the information being based upon the results of the mathematical probability estimate.

20 Claims, 11 Drawing Sheets

(51) Int. Cl.
| | |
|---|---|
| *G16H 15/00* | (2018.01) |
| *G16H 40/20* | (2018.01) |
| *G06Q 10/10* | (2012.01) |
| *G06Q 50/22* | (2018.01) |
| *G06Q 50/24* | (2012.01) |

(52) U.S. Cl.
CPC ............. *G16H 15/00* (2018.01); *G16H 40/20* (2018.01); *G16H 50/20* (2018.01)

(58) Field of Classification Search
CPC ........ G16H 10/20; G16H 10/40; G16H 10/65; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/40; G16H 40/60; G16H 40/63; G16H 40/67; G16H 50/00; G16H 70/00; G16H 70/20; G16H 70/40; G16H 70/60; G16H 80/00; G06Q 10/103; G06Q 50/24; G06Q 50/22

See application file for complete search history.

(56) References Cited

U.S. PATENT DOCUMENTS

| | | | | |
|---|---|---|---|---|
| 8,751,257 | B2* | 6/2014 | Amland | G06F 19/3431 |
| | | | | 705/2 |
| 9,934,361 | B2* | 4/2018 | Yao | G06Q 10/04 |
| 2004/0214011 | A1 | 10/2004 | Chang et al. | |
| 2011/0295613 | A1 | 12/2011 | Coyne | |
| 2011/0295622 | A1* | 12/2011 | Farooq | G06Q 10/10 |
| | | | | 705/3 |
| 2011/0313788 | A1 | 12/2011 | Amland et al. | |
| 2012/0004925 | A1* | 1/2012 | Braverman | G06F 19/325 |
| | | | | 705/2 |
| 2012/0271612 | A1 | 10/2012 | Barsoum et al. | |
| 2012/0296671 | A1* | 11/2012 | Simons-Nikolova | |
| | | | | G16H 40/20 |
| | | | | 705/2 |
| 2013/0085773 | A1 | 4/2013 | Yao et al. | |
| 2013/0096942 | A1* | 4/2013 | Bowles | G06F 19/00 |
| | | | | 705/2 |
| 2013/0132117 | A1 | 5/2013 | Barsoum et al. | |
| 2013/0191158 | A1* | 7/2013 | Fillmore | G06F 19/00 |
| | | | | 705/3 |

FOREIGN PATENT DOCUMENTS

| | | | | |
|---|---|---|---|---|
| WO | WO-2013022760 | A1 * | 2/2013 | ............. G16H 50/30 |
| WO | 2013084105 | | 6/2013 | |

OTHER PUBLICATIONS

Demir, et al., "Emergency Readmission Criterion: A Technique for Determining the Emeergency Readmission Time Window", IEEE Transactions on INformation Technology in Biomedicine, vol. 12, No. 5, Sep. 2008, pp. 644-649.

Novotny, "Clinical Prediction Model of Medical Inpatients at Risk of Early Readmission: Development and Validation", UMI Microform 3327513, 2008, University of Illinois at Chicago, pp. 1-252.

Escobar, et al., "Early Detection of Impending Physiologic Deterioration Among Patients Who Are Not in Intensive Care: Development of Predictive Models Using Data From an Automated Electronic Medical Record", Journal of Hospital Medicine, Journal of Hospital Medicine, vol. 000, No. 000, 2012, pp. 1-8.

Kassin, et al., "Risk Factors for 30-Day Hospital Readmission Among General Surgery Patients", American College of Surgeons, ISSN 10-72-7515/12, 2012, pp. 322-330.

Jencks SF, Williams MV, Coleman EA. Rehospitalizations among patients in the Medicare fee-for-service program. N Engl J Med. Apr. 2, 2009;360(14):1418-1428.

Office of Legislative Counsel. Compilation of the Patient Protection and Affordable Care Act.: U.S. House of Representatives, United States of America; 2010.

Mechanic R, Tompkins C. Lessons learned preparing for Medicare bundled payments. N Engl J Med. Nov. 15, 2012;367(20):1873-1875.

Horvitz E. From data to predictions and decisions: enabling evidence? based healthcare. Series on Data Analytics, Computing Community Consortium; Sep. 18, 2010.

Post AR, Harrison JH, Jr. PROTEMPA: a method for specifying and identifying temporal sequences in retrospective data for patient selection. Journal of the American Medical Informatics Association : JAMIA. Sep.-Oct. 2007;14(5):674-683.

Sittig DF, Singh H. Electronic health records and national patient-safety goals. N Engl J Med. Nov 8 2012;367(19):1854-1860.

Agency for Healthcare Research and Quality, U.S. Department of Health and Human Services, "HCUP Nationwide Inpatient Sample". http://hcupnet.ahrq.gov/HCUPnet.jsp Downloaded Dec. 14, 2012.

Bright, T.J., Wong, A., Dhurjati, R., Bristow, E., Bastian, L., Coeytaux, R.R., Samsa, G., Hasselblad, V., Williams, J.W., Musty, M.D., Wing, L., Kendrick, A.S., Sanders, G.D. and D. Lobach. 2012. "Effect of Clinical Decision-Support Systems," Annals of Internal Medicine 157(1): 29-44.

Caminiti, C., Meschi, T., Braglia, L., Diodati, F., Iezzi, E., Marcomini, B., Nouvenne, A., Palermo, E., Prati, B., Schianchi, T. and L. Borgis. 2013. "Reducing Unnecessary Hospital Days to Improve Quality of Care Through Physician Accountability: A Cluster Randomised Trial," BMC Health Services Research 13:14.

Center on Budget and Policy Priorities, 2013. "Policy Basics: Where Do Our Federal Tax Dollars Go?" Revised Apr. 12, 2013. http://www.cbpp.org/cms/?fa=view&id=1258.

Fuchs, V.R. and Millstein, A. 2011. "The $640 Billion Question— Why Does Cost-Effective Care Diffuse So Slowly?" New England Journal of Medicine, 2011, 364, 1985-1987.

Heggestad, Torhild. 2002. "Do Hospital Length of Stay and Staffing Ratio Affect Elderly Patients' Risk of Readmission? A Nation-Wide Study of Norwegian Hospitals," Health Services Research 37(3): 647-665.

Hunt, D.L., Haynes, R.B., Hanna, S.E., and K. Smith. 1998. "Effects of Computer-Based Clinical Decision Support Systems on Physician Performance and Patient Outcomes," Journal of the American Medical Association 280(15): 1339-1348.

Hwang, S.W., Li, J., Gupta, R., Chien, V. And R.E. Martin. 2003. "What Happens to Patients Who Leave Hospital Against Medical Advice?," Canadian Medical Association Journal 168: 417-420.

Institute of Medicine, National Academy of Sciences, Best Care at Lower Cost: The Path to Continuously Learning Health Care in America. Washington, DC: The National Academies Press, 2012.

Kaiser Health News, Oct. 2, 2012, "Medicare Revises Hospitals' Readmissions Penalties". http://www.kaiserhealthnews.org/Stories/2012/October/03/medicare-revises-hospitals-readmissions-penalties.aspx.

Lee, Eva K., Fan Yuan, Daniel A. Hirsh, Michael D. Mallory, and Harold K. Simmon. 2012. "A Clinical Decision Tool for Predicting Patient Care Characteristics: Patients returning within 72 Hours in the Emergency Department," AMIA Annual Symposium Proceedings: 495-504.

(56) References Cited

OTHER PUBLICATIONS

Leeds, Ira, Sadiraj, Vjollca, Cox, James C., Schnier, Kurt E. and Sweeney, John F. 2013. "Assessing Clinical Discharge Data Preferences among Practicing Surgeons," Journal of Surgical Research, in press.

Nabagiez, John P., Masood A. Shariff, Muhammad A. Khan, William J. Molloy, and Joseph T. McGinn. 2013. "Physician assistant home visit program to reduce hospital Readmissions." Journal of Thoracic and Cardiovascular Surgery 145(1): 225-233.

Office of Information Products and Data Analytics, Centers for Medicare and Medicaid Services, "National Medicare Readmission Findings: Recent Data and Trends," 2012. http://www.academyhealth.org/files/2012/sunday/brennan.pdf.

Organization for Economic Cooperation and Development, "OECD Health Data 2012: How Does the United States Compare". http://www.oecd.org/unitedstates/BriefingNoteUSA2012.pdf Downloaded Dec. 14, 2012.

Roth, A.E., Sönmez, T. and M.U. Ünver. 2004. "Kidney Exchange," Quarterly Journal of Economics 119(2), 457-488.

Shea, S.; R. V. Sideli; W. DuMouchel; G. Pulver; R. R. Arons and P. D. Clayton. 1995. "Computer-Generated Informational Messages Directed to Physicians: Effect on Length of Hospital Stay," Journal of the American Medical Informatics Association 2(1), 58-64.

Hernandez AF, Curtis LH. Minding the gap between efforts to reduce readmissions and disparities. Jama Feb. 16, 2011;305(7):715-716.

Axon RN, Williams MV. Hospital readmission as an accountability measure. Jama. Feb. 2, 2011;305(5):504-505.

Tanenbaum SJ. Knowing and acting in medical practice. In: Lindemann J, ed. Meaning and Medicine: A reader in the philosophy of health care. New York, NY: Routledge; 1999.

Mulley AG, Wennberg JE. Reducing unwarranted variation in clinical practice by supporting clinicians and patients in decision-making. In: Gigerenzer G, Muir JA, eds. Better Doctors, Better Patients, Better Decisions. Cambridge, MA: MIT Press; 2011:45-52.

Andriole DA, Jeffe DB, Schechtman KB. Is surgical workforce diversity increasing? J Am Coll Surg. Mar. 2007;204(3):469-477.

Amarasignham, R., Moore, B.J., Tabak, Y.P., Drazner, M.H., Clark, C.A., Zhang, S., Reed, W.G., Swanson, T.S., Ma, Y. and E.A. Halm. 2010. "An Automated Model to Identify Heart Failure Patients at Risk for 30-Day Readmission or Death Using Electronic Medical Record Data," Medical Care 48(11): 981-988.

Anderson, Gerard F., and Earl P. Steinberg. 1985. "Predicting Hospital Readmissions in the Medicare Population," Inquiry 22(3): 251-258.

Anderson, D., Golden, B., Jank, W., Price, C. and E. Wasil. 2011. "Examining the Discharge Practices of Surgeons at a Large Medical Center," Health Care Management Science 14(4): 338-47.

Anderson, D., Golden B., Jang, W. and E. Wasil. 2012. "The Impact of Hospital Utilization of Patient Readmission Rate," Health Care Management Science 15(1): 29-36.

Bowles, K.H., Foust, J.B. and M.D. Naylor. 2003. "Hospital Discharge Referral Decision Making: A Multidisciplinary Perspective," Applied Nursing Research 16(3): 134-43.

Demir, E. 2012. "A Decision Support Tool for Predicting Patients at Risk of Readmission: A Comparison of Classification Trees, Logistic Regression, Generalized Additive Models, and Multivariate Adaptive Regression Spline," Working Paper, University of Hertfordshire Business School.

Graumlich, J.F., Novotny, N.L., Nace, G.S. and J.C. Aldag. 2009a. "Patient and Physician Perceptions After Software-Assisted Hospital Discharge: Cluster Randomized Trial," Journal of Hospital Medicine 4(6): 356-363.

Graumlich, J.F., Novotny, N.L., Nace, G.S., Kaushal, H., Ibrahim-Ali, W., Theivanayagam, S., Scheibel, L.W. and J.C. Aldag. 2009b. "Patient Readmission, Emergency Visits, and Adverse Events After Software-Assisted Discharge From Hospital: Cluster Randomized Trial," Journal of Hospital Medicine 4(7): E11-E19.

Roth, A.E., Sönmez, T. and M.U. Ünver. 2007. "Efficient Kidney Exchange: Coincidence of Wants in Markets with Compatibility-Based Preferences," American Economic Review 97(3), 828-51.

Smith RSW. The chasm between evidence and practice: extent, causes, and remedies. In: Gigerenzer G, Muir JA, eds. Better Doctors, Better Patients, Better Decisions. Cambridge, MA: MIT Press; 2011:265-280.

Cox, J.C., et al., Incentivizing cost-effective reductions in hospital readmission rates. J. Econ. Behav. Organ. (2015), http://dx.doi.org/10.1016/j.jebo.2015.03.014.

Cox, J.C., et al., Higher quality and lower cost from improving hospital discharge decision making. J. Econ. Behav. Organ. (2015), http://dx.doi.org/10.1016/j.jebo.2015.03.017.

* cited by examiner

SYSTEMS AND METHODS FOR SUPPORTING HOSPITAL DISCHARGE DECISION MAKING

CROSS-REFERENCE TO RELATED APPLICATION

This application is the 35 U.S.C. § 371 national stage application of PCT Application No. PCT/US2014/036609, filed May 2, 2014, which claims priority to U.S. Provisional Application Ser. No. 61/819,130, filed May 3, 2013, both of which are herein incorporated by reference in their entirety.

NOTICE OF GOVERNMENT-SPONSORED RESEARCH

This invention was made with Government support under grant/contract number 1RC4AG039071-01, awarded by the National Institutes of Health, National Institute on Aging. The Government has certain rights in the invention.

BACKGROUND

In 2010 Americans spent 17.6 percent of gross domestic product (GDP) on healthcare, which was eight percentage points above the Organization for Economic Cooperation and Development (OECD) average. Medicare, Medicaid, and the Children's Health Insurance Program (CHIP) spending alone made up 21 percent of the 2012 federal budget (Center on Budget and Policy Priorities, 2013). American healthcare is by far the most expensive in the world, yet the quality patients receive from this investment is somewhere near the middle of the pack when compared to other economically developed nations (Fuchs and Millstein, 2011). Recent estimates suggest that the amount of wasted, excess costs in healthcare were $765 billion for 2009, which was $100 billion more than the entire Department of Defense budget for that year (Institute of Medicine, 2012). In order to curb such expenses, the cost of care needs to decrease and the quality of care needs to increase.

The length of a patient's hospital stay, referred to in the industry as the length of stay (LOS), is a fundamental factor in the increasingly important and complex interplay between the quality of healthcare delivery and medical costs. The inpatient environment bolsters the intensity of care and longer hospital stays have been associated with a lower incidence of adverse outcomes leading to readmissions (Heggestad 2002). However, the hospital is also an exceptionally expensive care delivery environment. The objective of decreasing medical costs, or at least reducing their outsized rate of increase, would be well served by reducing LOS. If the average LOS could be reduced by just 5 percent, the savings would exceed $64 billion. However, lower LOS may lead to higher hospital readmission rates, which is a focus of concern of Medicare.

Hospital readmissions have recently become a critical healthcare quality metric for American hospitals. In 2010, 19.2 percent of Medicare patients were readmitted within 30 days of discharge, resulting in additional hospital charges totaling $17.5 billion (Office of Information Products and Data Analytics, 2012). Hospitals and physicians are encountering increasing pressure to reduce hospital readmission rates, both from reputation effects from public disclosure of performance and pay-for-performance reimbursement schemes that refuse payment for related readmissions.

Surgical patient readmissions can be triggered by post-operative complications (e.g. surgical wound infections), aggravation of comorbidities (e.g. diabetes or heart disease), poor transitions of care from the in-patient to out-patient setting, or low quality post-discharge healthcare. One approach that could reduce readmissions would be to increase LOS; however, significantly increasing LOS would jeopardize the financial viability of a hospital because of capitated payments by Medicare and insurance companies. Regardless of whether a patient stays in a hospital for two days or two months, the hospital gets paid the same amount for the care with capitation contract insurance. Hence, the challenge is to decrease LOS without simultaneously increasing readmission rates.

Despite the critical nature of the inpatient stay, responsibility for the discharge decision currently resides with practicing physicians and is largely a subjective decision. Although guidelines for LOS for specific diagnostic-related groups exist, it would be desirable to improve hospital discharge decision making by providing the physician with an objective indication of the likelihood of an individual patient being readmitted to the hospital if he or she were discharged. More particularly, it would be desirable to provide such an indication that is based upon the patient's own idiosyncratic susceptibility to complications and his or her own specific comorbidities.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

Figure 1:
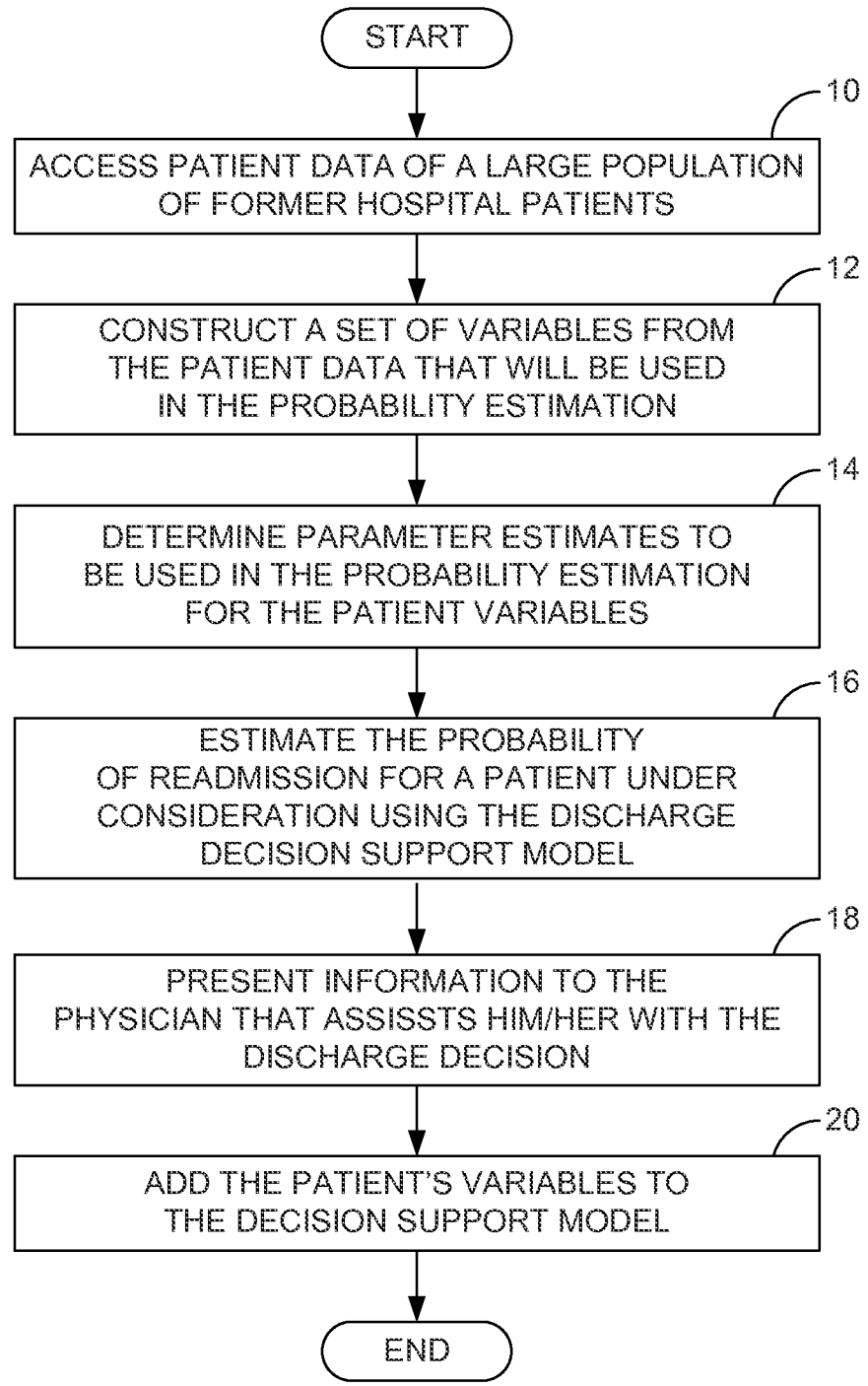
FIG. 1 is a flow diagram of an embodiment of a method for assisting a physician with a hospital discharge decision.

As described above, it would be desirable to improve hospital discharge decision making by providing the physician with an objective assessment of the likelihood of an individual patient being readmitted to the hospital that is based upon the patient's own idiosyncratic susceptibility to complications and the patient's own specific comorbidities. Disclosed herein are systems and methods that serve this purpose. In some embodiments, the systems and methods identify the probability of a patient under consideration being readmitted to the hospital within a predetermined period of time (e.g., 30 days) if the patient were discharged on that day. The probability is determined using a discrete choice model that has been calibrated with historical patient data that has been collected from a large population of previous patients. The model is able to determine this probability because the outcomes for the previous patients (i.e., whether or not the patient was readmitted) are known. In some embodiments, the systems and methods take into account not only vital patient data that is measured during the hospital stay such as heart rate, temperature, etc., but also other patient data that are statistically-significant predictors of readmission, such as lab results, administered medicines, and demographics. In some embodiments, the probability of readmission is periodically recalculated (e.g., daily). Because the probability can change as new patient data is collected, the physician can be provided with an indication of the likelihood that the patient will be readmitted if the patient were discharged as to each particular day of the hospital stay, which is based upon the most up-to-date information that is available. In some embodiments, the most statistically-significant patient data can be presented to the physician along with the probability information to further assist the physician with the discharge decision.

In the following disclosure, various specific embodiments are described. It is to be understood that those embodiments are example implementations of the disclosed inventions and that alternative embodiments are possible. All such embodiments are intended to fall within the scope of this disclosure.

The incidence of readmission can be reduced and hospital length of stay (LOS) shortened by utilization of better discharge criteria for individual patients. LOS can be decreased without increasing readmission rates through use of decision support information technology. Physicians have rapidly increasing access to large amounts of data on each patient they treat through electronic medical record (EMR) systems. The problem for improving discharge decision making is not shortage of data on the patient, but rather absence of evidence-based discharge criteria that can be effectively applied in making the discharge decision.

The current practice is that a patient remains in the hospital unless a physician with authority to discharge the patient completes "discharge orders." Prior to deciding whether to discharge the patient, a physician will examine the patient, review EMRs for the patient, and perhaps consult with one or more colleagues. Criteria applied to making a discharge decision are derived from the physician's recall of his or her medical education and own previous practice and, perhaps, discussions with colleagues. This evidence base is extremely limited by comparison to the information that could be derived from the EMRs of the hospital's patient population. A large teaching hospital, for example, will serve on the order of 20,000 to 40,000 patients per year. Each surviving patient will be discharged from the hospital and it will subsequently be revealed, in most cases, whether the discharge was successful or unsuccessful (i.e., led to readmission within 30 days). This suggests the following question: Do the data profiles for patients who are successfully discharged differ in identifiable ways from the data profiles for patients who are unsuccessfully discharged? If the answer to this question is "yes", then that would open the possibility of building decision support software that can inform discharge decisions for individual patients with the accumulated experience acquired from discharging thousands of other patients.

As is described below, a discrete choice model that has been calibrated with a large sample of data from patient EMRs can form the foundation for a hospital discharge decision support model that uses data collected from an individual patient under consideration over the course of his or her stay in a hospital to generate patient-specific, day-specific probabilities of readmission. The discharge decision support model can present the physician with the estimated daily readmission probabilities (with error bounds) and dynamically-selected patient variables in a user-friendly format to assist the physician with his or her decision.

FIG. 1 is a flow diagram that provides an overview of an example method for assisting a physician with a hospital discharge decision using a hospital discharge decision support model. Beginning with block 10 of FIG. 1, patient data of a large population of former hospital patients is accessed. The patient data can, for example, be obtained from EMRs. As is discussed below, the patient data can include many different pieces of information relating not only to vital patient data that is measured during the hospital stay but also other patient data that may also be predictive of readmission, such as, lab results, administered medicines, and demographics. In some embodiments, the population may all share a common medical condition. For example, the former patients each may have been hospitalized because of a cardiac issue or because of a gastrointestinal issue. In such cases, the model can be specifically configured to estimate the probability of readmission for a specific type of patient. In other embodiments, the patients need not share a medical condition. In such a case, the system can be used to estimate the probability of readmission for substantially any hospital patient.

Turning to block 12, a set of variables is constructed that is based on the accessed patient data and will be used in the probability of readmission estimation. As discussed below, these variables represent the core pieces of information that are most predictive of whether or not a patient will be readmitted to the hospital within a predetermined period of time (e.g., 30 days). In some cases, a variable can be the same as a piece of patient data. In other cases, the variable can be derived from patient data.

Referring next to block 14, parameter estimates that will be used to calibrate the discharge decision support model are determined. In some embodiments, the parameter estimates comprise the coefficients that are applied to the patient variables and account for their relative statistical significance in predicting whether or not the patient will be readmitted. In some embodiments, as is discussed below, the parameter estimates can be determined using an iterative process in which the least statistically significant variables (and associated parameter estimates) are removed from the model.

Once the parameter estimates have been determined, the probability of readmission for a patient under consideration, i.e., a current patient staying at the hospital, can be estimated using the discharge decision support model, as indicated in block 16. This estimation is performed using the parameter estimates determined in block 14 and the patient under consideration's own patient variables, which are of the same nature as the aforementioned patient variables. Through this estimation, a probability (e.g., in the form of a number between 0 and 1) can be obtained that provides an indication of the probability that the patient will be readmitted within the predetermined period of time if the patient is discharged on that day.

At this point, information can be provided to the physician in charge of making the discharge decision that can assist him or her with that decision, as indicated in block 18. As is discussed below, this information can take a variety of forms. In some embodiments, the readmission probability on each day of the patient's hospital stay is plotted in a graph so that the physician can track the progression of this probability, whether it has decreased, increased, or stayed the same. A confidence interval can also be displayed along with the probability estimates to give the physician an indication of the error bounds. In addition, a target probability can be displayed in the graph so that the physician can compare the current day's estimate and/or confidence interval with the target probability. In some embodiments, the patient data (e.g., clinical data) most predictive on that day of whether or not the patient will be readmitted within the predetermined time period can also be presented to the physician to further assist him or her with the discharge decision.

With reference to block 20, the patient under consideration's data can at some point (e.g., after discharge) be added to the collection of patient data referred to in relation to block 10. In this manner, the database upon which the probability estimations are determined can be continually updated with new information, if desired.

Figure 2A:
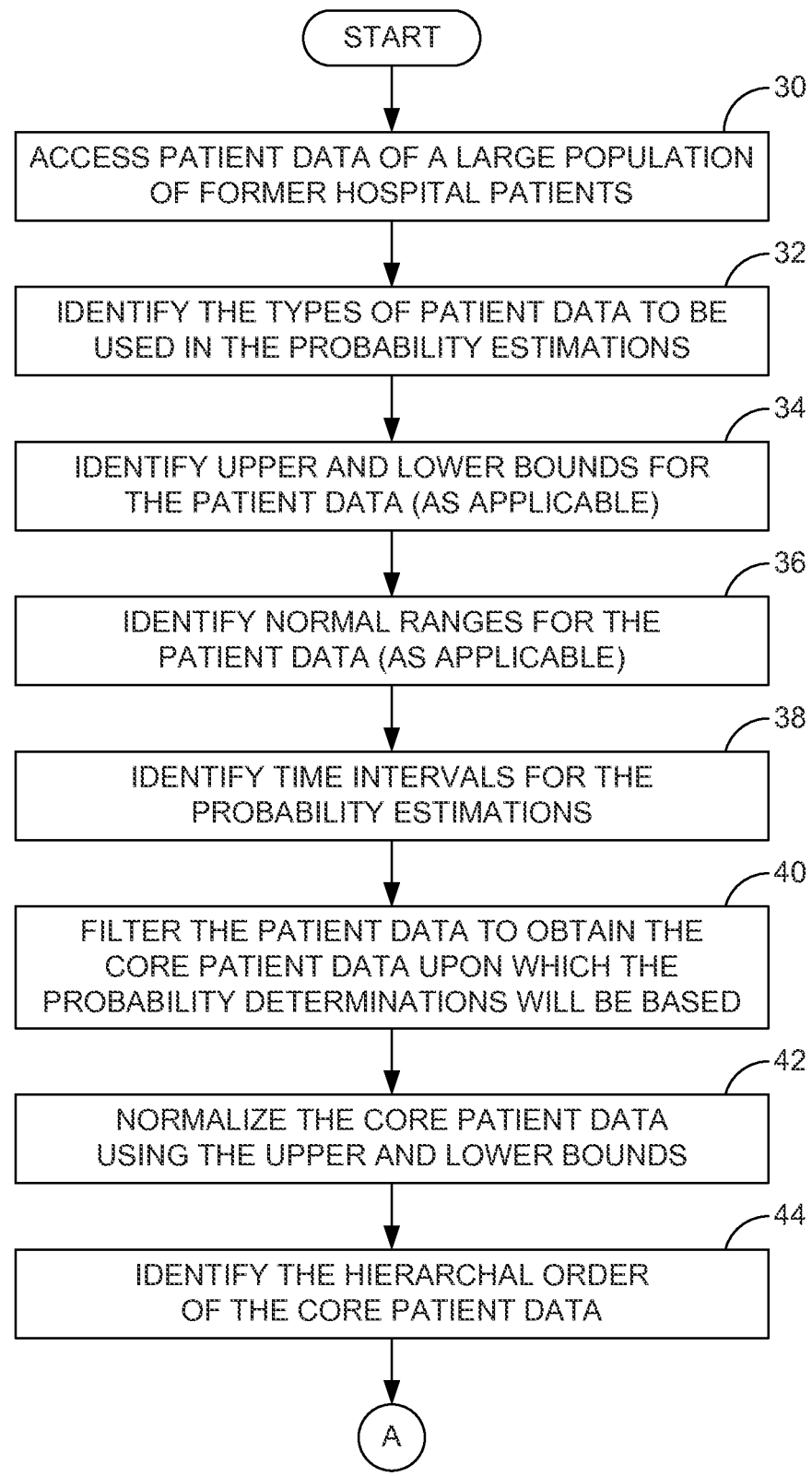
FIGS. 2A-2C comprise a flow diagram of an embodiment of a method for constructing a hospital discharge decision support model.

Having provided an overview of assisting a physician with a discharge decision, an embodiment of a method for constructing a hospital discharge decision support model will now be discussed in relation to FIGS. 2A-2C. Beginning with block 30 of FIG. 2A, patient data of a large population of former patients is accessed. As noted above in relation to FIG. 1, the patient data can, for example, be obtained from EMRs. In such a case, all patients can be assigned a unique patient identification number that links their data across different subsets of data. A patient's stay defines the time stamping used in the data sets. For instance, the patient's first day can be identified as day 0-1, day two can be identified as day 1-2, etc. Therefore, each new piece of data to be recorded can be tagged with a time stamp that identifies when the data was obtained.

As was also noted above, the patient data can include many different pieces of information. In some embodiments, the patient data includes one or more of diet data, imaging data, lab data, medicine data, nurse data, patient-specific data, transfusion data, and vital data. The diet data can include a time stamp for when a diet order is made and whether the patient is on a nothing per orem (NPO), clear liquids, full liquids, or solids diet. The imaging data can include the type of any imaging requested as defined by the imaging codes used internally by the hospital. This information is also time stamped by the day of the patient's stay. The lab data can include the results of any lab test, such as albumin, bilirubin, blood urea nitrogen (BUN), creatinine, hematocrit (HCT), platelet count, prothrombin time (PT), partial thromboplastin time (PTT), sodium, and white blood cell (WBC) count. The medicine data can include a time-stamped order for any drug that was prescribed for the patient during their stay and its drug category (an internal hospital code). In addition, the medicine data can include the manner in which the medicine was administered (e.g., by mouth, intravenously). The nurse data can include the fall risk score, Katz total score, and stool count output that a nurse recorded along with a time stamp. The patient-specific data includes the data that does not vary during the course of the patient's stay as well information relating to the length of stay and whether or not the patient was readmitted in the predetermined time period. The patient-specific data can include the following coded information:

PATIENT_ID: patent identification
PT_AGE: patent age
ETHNICITY: patient ethnicity
GENDER: patient gender
HOSPITAL_NM: hospital name
SOURCE_ADMIT_HOSPITAL_DESC: source of admission
TYPE_ADMIT_HOSPITAL_DESC: type of hospital admission
ADMIT_TO_SERVICE_DAYS: days from admit to service
PROCEDURE_CPT_CD: current procedural terminology code
PROCEDURE_CPT_DESC: description of the procedure
DAYS_TO_READMIT: days to readmit if readmitted following service
WORK_RVUS: work relative value units
PATIENT_DEATH_DT: date of patient's death if deceased
LOS: patient's length of stay
DIABETES_FLAG: indicator for diabetes
DISS_CANCER_FLAG: indicator for cancer
HYPERTENSION_FLAG: indicator for hypertension
ASCITES: indicator for ascites
CHD: indicator for congenital heart defect
ALCOHOL_FREQ: frequency of alcohol use
ALCOHOL_USE: binary indication for alcohol use
ALCOHOL_AMT: amount of alcohol use
TOBACCO_USE: binary indication for tobacco use
TRACT: the census tract in which the patient lives
DISTANCE: the distance to hospital for the patient The transfusion data can include a time-stamped order for a transfusion during the patient's stay that identifies when the transfusion was ordered. Finally, the vital data can include data related to body mass index (BMI), diastolic blood pressure (BP), functional status, heart rate (HR), oxygen saturation, pain score, respiration rate, systolic BP, and body temperature, as well as a time stamp for when each was recorded.

As can be appreciated from the above discussion, there are many different types of patient data upon which the probability estimation can be based. Not all of these types of data are useful in all situations. For example, certain types of data will be less indicative of the likelihood of readmission for certain types of patients. In view of this, the particular types of patient data that are to be used in the probability estimations can be identified, as indicated in block 32. In some embodiments, these types of data can be identified with the assistance of an experienced physician who can identify, e.g., from a list of the types of patient data, which patient data can be prioritized for the estimation.

In addition to identifying the types of patient data to be used, the upper and lower bounds and the normal ranges for the patient data can be identified (as applicable), as indicated in blocks 34 and 36, respectively. For example, if the patient data under consideration is body temperature, the upper and lower bounds can denote the maximum and minimum temperatures possible for a living human being (e.g., 115° F. and 75° F.) and the normal range can be the range of temperatures of a healthy human being (e.g., 97° F. to 100° F.). The upper and lower bounds can be used to discard outlier (e.g., erroneous) data and, as described below, to normalize all of the patient data. As is also described below, the normal ranges can be used to construct patient variables that will be used in the probability estimations. As before, the bounds and the normal ranges can be identified with the assistance of an experienced physician.

Referring next to block 38, the intervals for the probability estimations, i.e., the time intervals upon which the probability of the patient being readmitted will be estimated, can also be identified. In some embodiments, this is a user-selectable aspect of the system. By way of example, the intervals can be a whole fraction of a 24 hour period (e.g., 8 hr. intervals).

Once the various types of information described in relation to blocks 32-38 has been identified, the patient data can be filtered to obtain the core patient data upon which the probability determinations will be based, as indicated in block 40. This filtering can include removal of particular types of patient data as well as removal of outlier data that is likely erroneous and could skew the results. At this point, the core patient data can be normalized using the upper and lower bounds, as indicated in block 42. When such normalization is performed, the various types of data each have the same scale and therefore each can be considered in making the probability estimation. In some embodiments, the data is normalized so that each piece of data is a number between 0 and 1.

In addition to normalizing the core patient data, the hierarchal order of the data can be identified, as indicated in block 44. In some embodiments, each piece of patient data can be ranked relative to the other pieces of data in relation to their perceived usefulness in making a discharge decision. Again, an experienced physician can be consulted to assist with this process. As is discussed below, establishing the hierarchal order assists in the elimination of patient variables from the model.

Figure 2B:
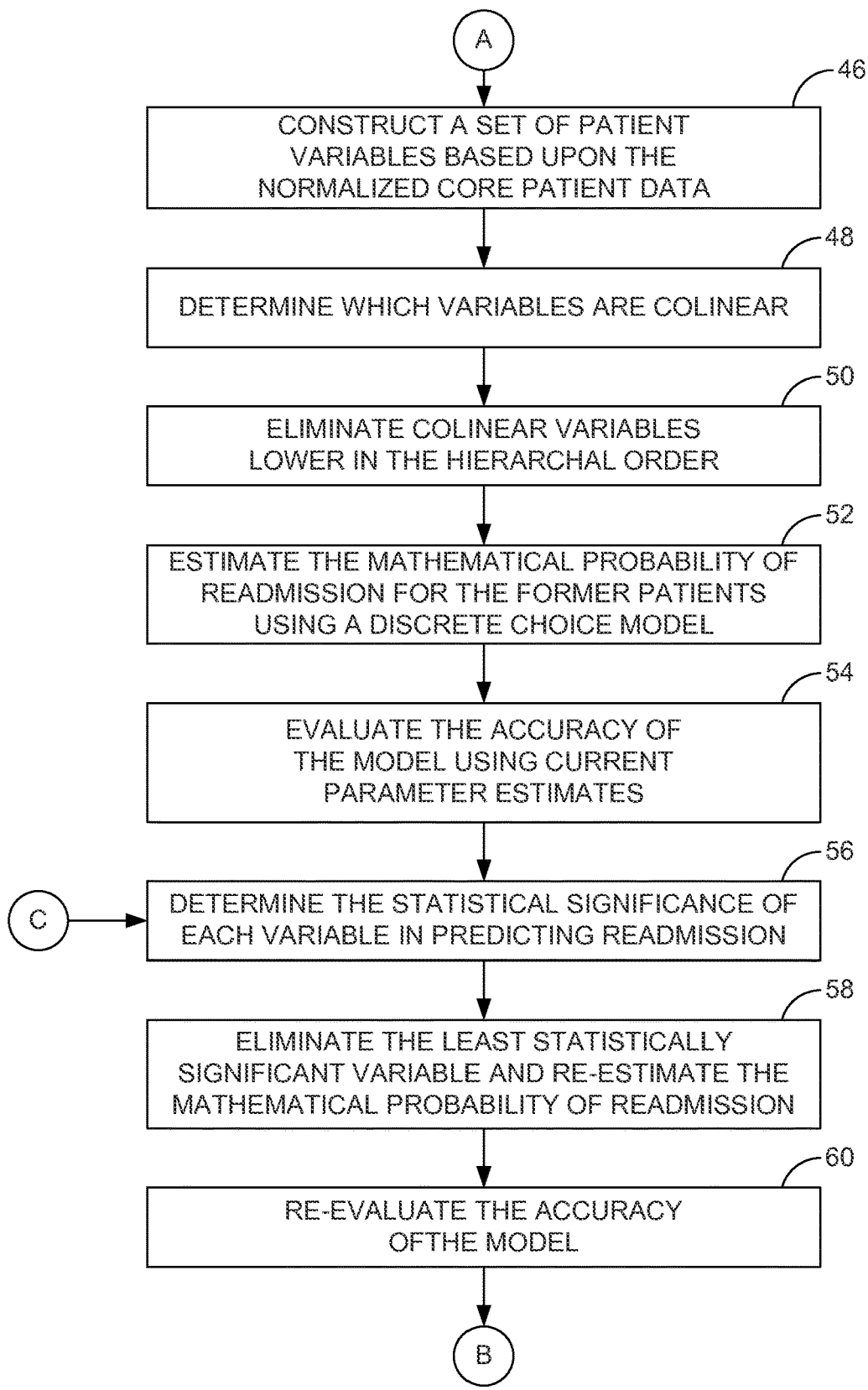
Figure 2C:
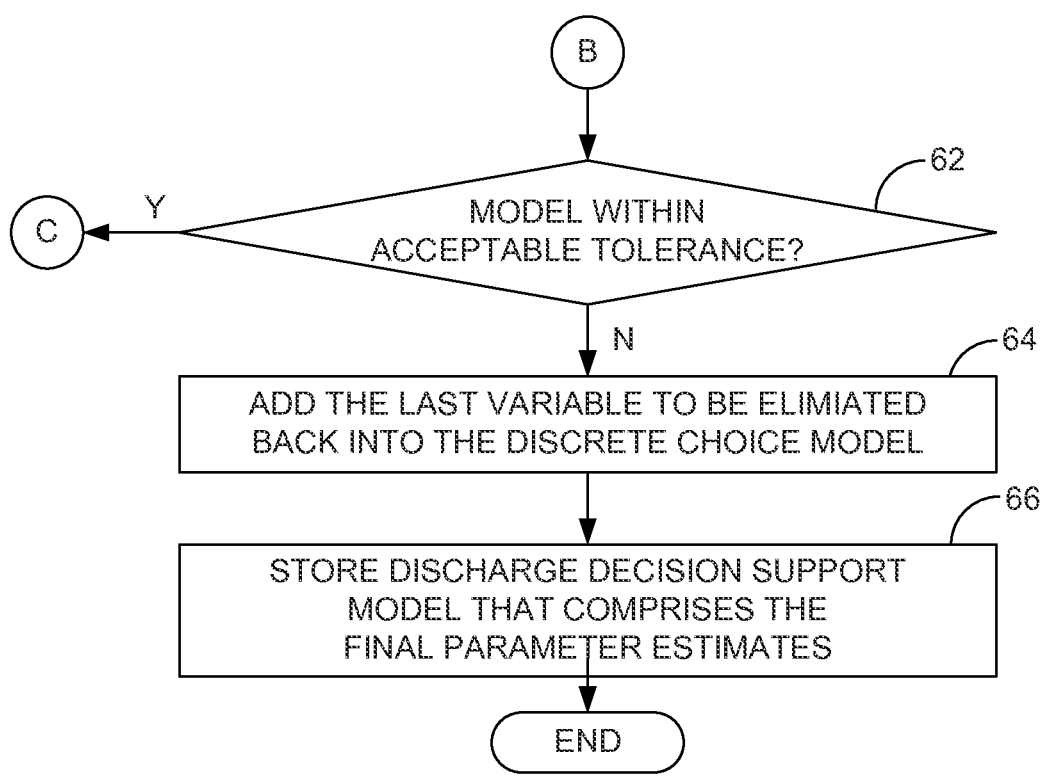

Turning to block 46 of FIG. 2B, a set of patient variables that will be used in the probability estimation can be constructed based upon the normalized core patient data. As mentioned above in relation to FIG. 1, some of the variables can be the same as individual pieces of patient data. Other variables, however, are pieces of data that are derived from the patient data. In some cases, a variable can be an interaction of two or more pieces of patient data, such as the interaction of the patient's body temperature and heart rate. In addition, a variable can be a time-constructed variable that relates a piece of patient data with time, such as the number of days that a patient's body temperature has been in the normal range or the minimum and/or maximum value that was observed over a particular number of days.

Through such construction, several hundred different patient variables can be created that are available for use in the probability estimation. While each of these variables can be used, some of them may be collinear with each other. Because such colinearity can skew the results, the variables that are collinear can be determined (block 48) and the collinear variables lower in hierarchal order can be eliminated (block 50). In some embodiments, colinearity can be identified by performing linear correlations and constructing a correlation matrix. A correlation tolerance can be established above which a collinear variable is to be eliminated. In some embodiments, the correlation tolerance can be 0.9. Through this elimination, the number of variables to consider may be reduced.

At this point, the mathematical probability of readmission can be estimated for the former patients using a discrete choice model, as indicated in block 52. Because the actual outcome of these former patients, in terms of whether or not they were readmitted, is known, the ability of a model to predict the outcome can be evaluated. Different models can be used to estimate the probability. Example models include a probit model, a logit model, a support vector machine (SVM) with alternative kernel specifications (such as Gaussian, polynomial, hyperbolic tangent), a neural network model with one or more hidden layers, a Bayesian Markov chain Monte Carlo (MCMC) model, a method of moments model, a simulated method of moments model, an expectation maximization (EM) algorithm, and a linear probability model. Irrespective of the model that is used, probability of readmission within the predetermined time is estimated for each of the former patients. In addition, parameter estimates are generated that are the coefficients that are applied to the patient variables (i.e., the variables are multiplied by the parameter estimates) in the model to account for the relative statistical significance of the variables in predicting whether or not the patient will be readmitted.

Once the probabilities have been estimated, the accuracy of model, as applied using the current parameter estimates, is evaluated, as indicated in block 54. In some embodiments, the model can be evaluated, within the sample and out of the sample, using a model fit estimate, such as log-likelihood, C-statistic, receiver operator curve (ROC), Brier score, F-score (for skewed data), precision, or sensitivity. The result of this evaluation can then be stored for future reference and use in specific embodiments of model selection.

Referring next to block 56, the statistical significance of each patient variable in predicting readmission can be determined. In some embodiments, this can be accomplished by using a t-test. Once the statistical significance of the variables is known, in some embodiments the least significant variable can be eliminated (block 58) and the accuracy of the model can be re-evaluated (block 60). This accuracy can be compared to the results determined in relation to block 54. For example, if the log-likelihood test was used, a likelihood ratio test can be performed. Referring to decision block 62 of FIG. 2C, if through such comparison the model is determined to predict readmission with an acceptable level of tolerance, the eliminated variable is not needed in the probability estimation. In such a case, flow returns to block 56 of FIG. 2B at which the next least significant variable is eliminated and the evaluation is repeated. In some embodiments, this process continues in an iterative fashion with variables being eliminated from the model until the model can no longer predict readmission with the acceptable level of tolerance. In some embodiments, flow then continues to block 64 of FIG. 2C and the last variable to be eliminated is added back into the discrete choice model.

At this point, the core patient variables and the final parameter estimates have been determined so as to create a discharge decision support model that can be applied to new patient data. By way of example, the number of patient variables can, in some embodiments, be reduced through the above-described process to approximately 100-200 core patient variables. The model can then be stored, as indicated in block 66, for later use.

Having described creation of the decision support model, application of the model to assist a physician with a hospital discharge decision will now be described in relation to FIG. 3.

Figure 3:
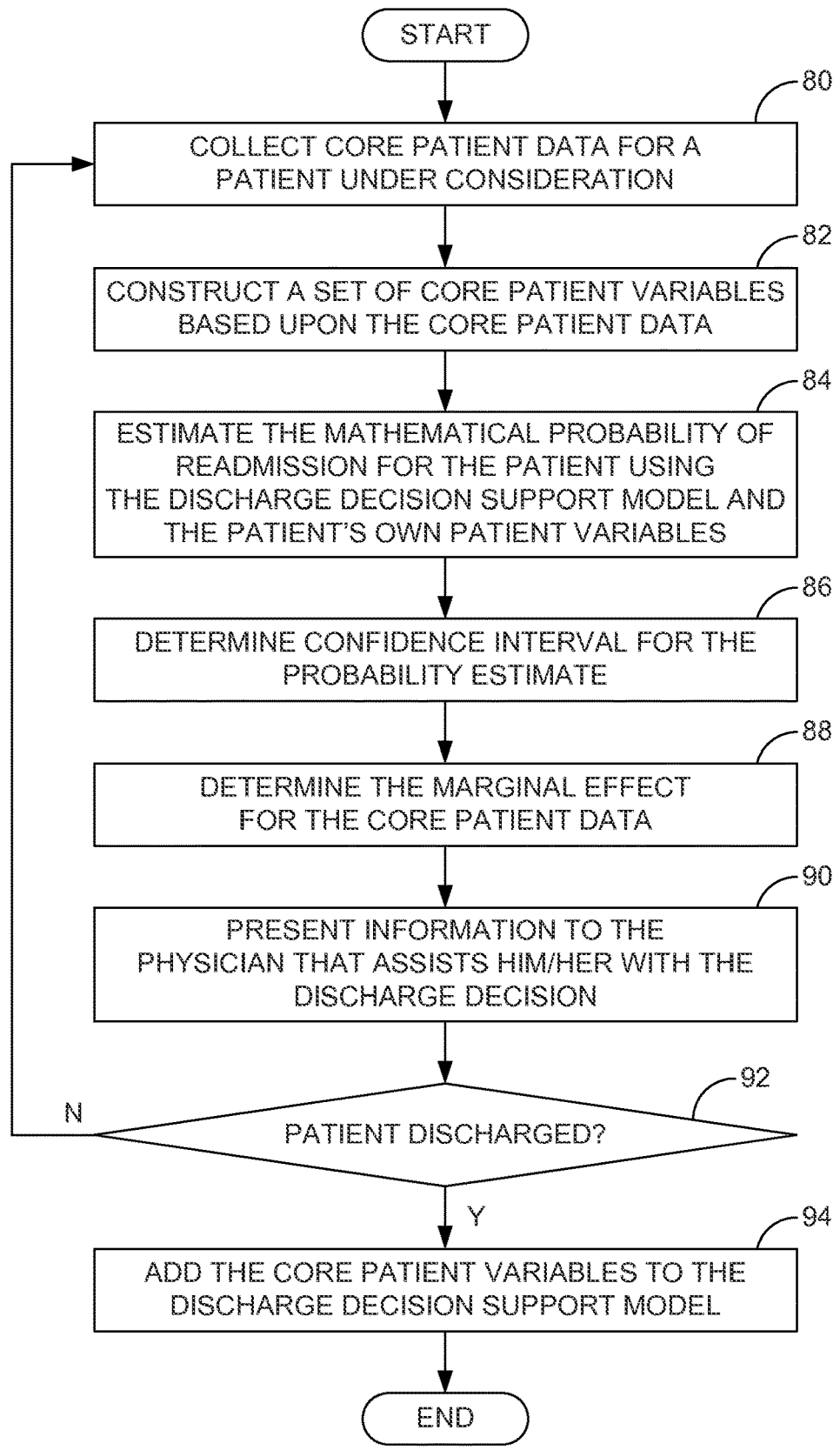
FIG. 3 is a flow diagram of an embodiment of a method for assisting a physician with a hospital discharge decision using the discharge support model described in relation to FIG. 2A-2C.

Beginning with block 80 of FIG. 3, core patient data is collected for a patient under consideration in association with his or her hospital stay. The data that is collected is the same type of data as the core patient data that was used to build the discharge decision support model described above. From this core patient data, a set of core patient variables is constructed, as indicated in block 82. These variables are the same core patient variables that were used to build the discharge decision support model.

At this point, the mathematical probability of readmission for the patient under consideration can be estimated using the discharge decision support model and the patient's own patient variables, as indicated in block 84. A probability estimate results that estimates the probability of the patient under consideration to be readmitted within the predetermined time period if he or she were discharged on the current day.

In addition to the probability estimate, a confidence interval can be determined for the probability estimate. In some embodiments, the confidence interval is a user setting that can be selected by an appropriate person, such as the hospital administrator. By way of example, the confidence interval can be 80%. The marginal effect of each piece of patient data can also be determined, as indicated in block 88. This provides an indication as to which data being collected is most useful in making the discharge decision. In some embodiments, the marginal effect is calculated by taking the derivative of the estimated model with respect to each variable.

Figure 4:
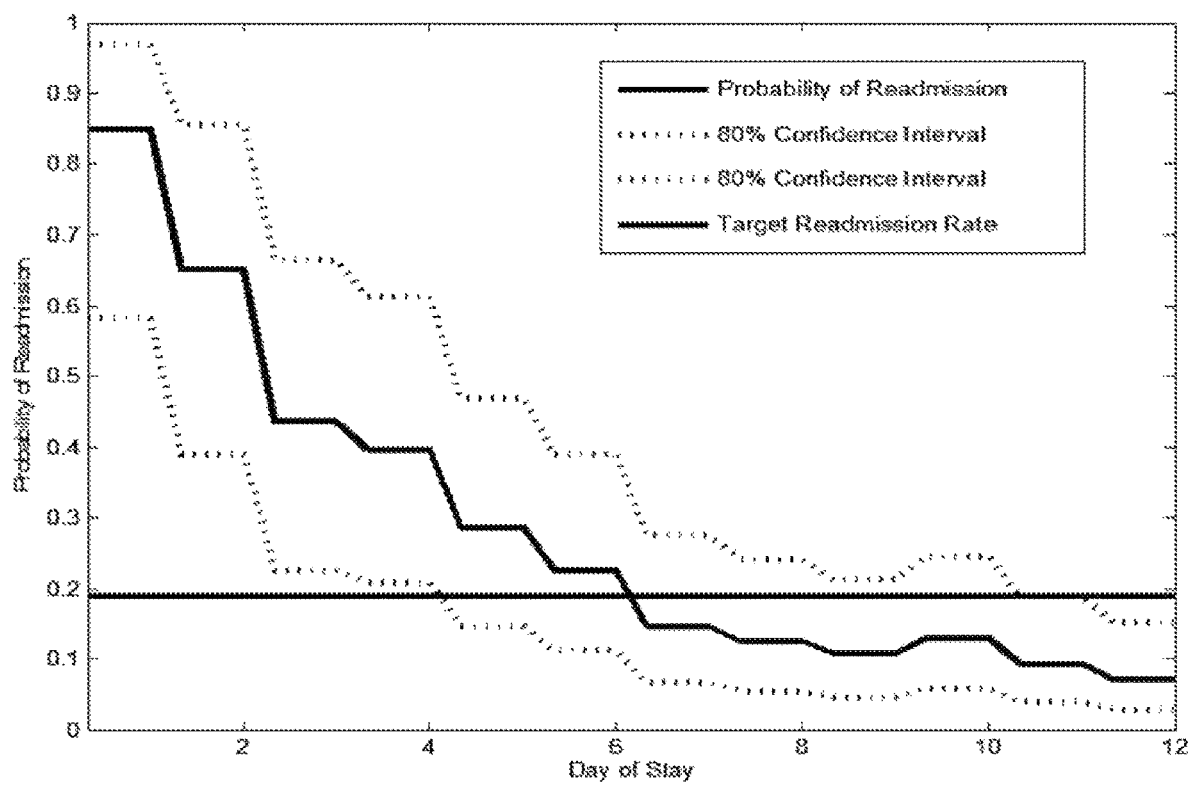
FIG. 4 is a graph that plots an estimated daily readmission probability for a patient under consideration.

Once the above-described results have been determined, information can be presented to the physician to assist him or her with the discharge decision, as indicated in block 90. As mentioned above, this information can take a variety of forms. In some embodiments, the probability estimates for each day of the patient's hospital stay are plotted in a graph so that the physician can track the progression of this probability. FIG. 4 shows an example of such a graph. As indicated in FIG. 4, the x axis of the graph identifies the hospital stay days and the y axis of the graph identifies the probability estimate. In the example of FIG. 4, the probability estimate changed each day of the hospital stay as the patient data changed. The probability estimates are shown in FIG. 4 connected by a solid line that identifies the probability of readmission as a function of the patient's time in the hospital. Also included in the graph are dashed lines that represent the upper and lower bounds of an 80% confidence interval. These bounds define a "probability envelope" that can be consulted by the physician.

In addition to the probability estimates and the associated confidence intervals, the graph of FIG. 4 also includes a line for the target probability of readmission. In the example of FIG. 4, this target is approximately 0.19, which translates to a 19% probability that the patient will be readmitted to the hospital within the predetermined time period (e.g., 30 days). In some embodiments, it is recommended not to discharge the patient if, on any given day, the probability estimate is above the target probability of readmission. This is the case for days 1, 2, 3, 4, 5, and 6 in the example of FIG. 4. By contrast, it is recommended that the patient be discharged if, on any given day, the target probability of readmission is above the confidence interval. This is the case for day 12 in the example of FIG. 4. Finally, for days on which the target probability of readmission falls between the probability estimate and the upper end of the confidence interval, the decision as to whether or not to discharge can be left to the discretion of the physician. This is the case for days 7, 8, 9, 10, and 11 in the example of FIG. 4.

Figure 5A:
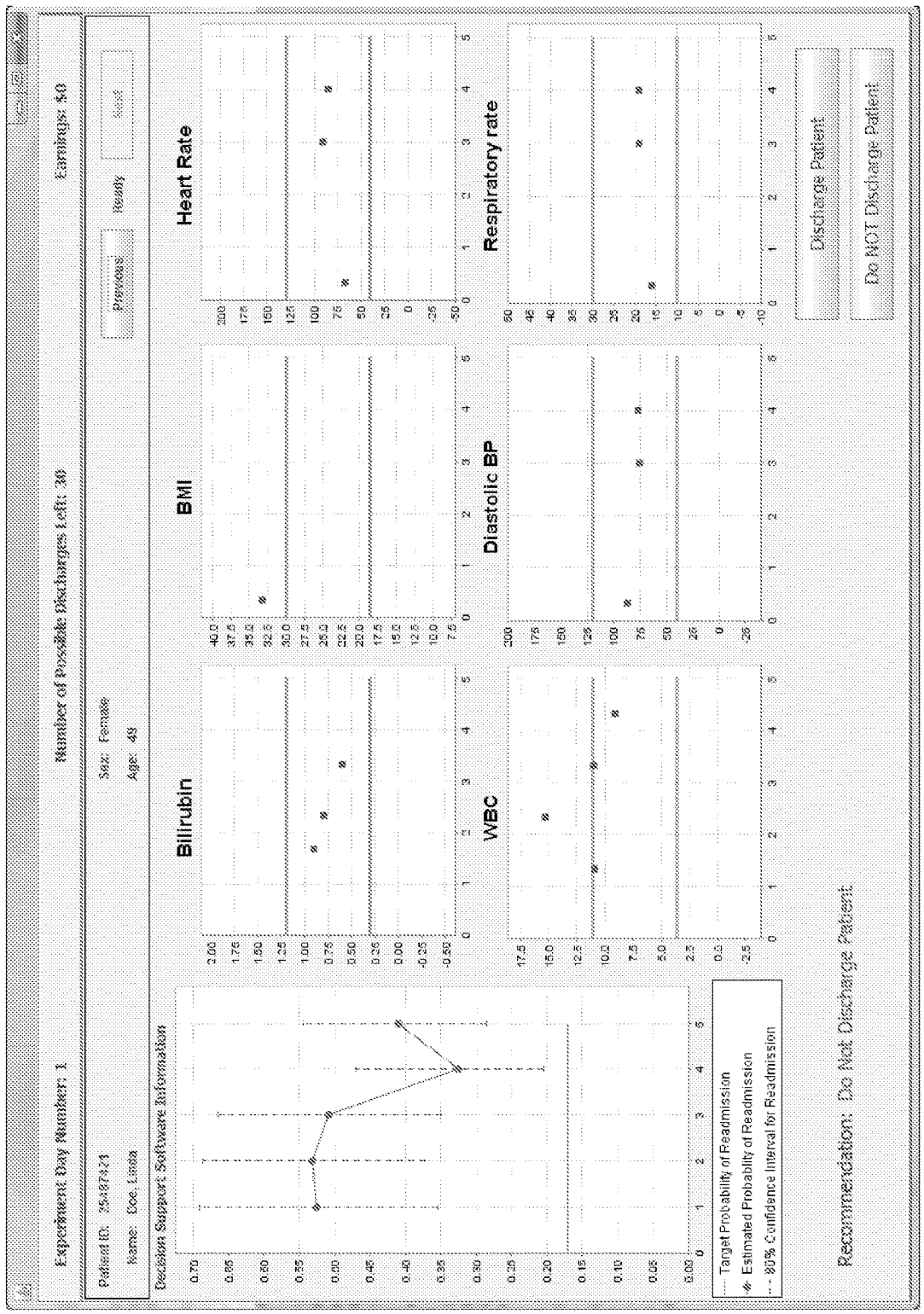
FIGS. 5A-5C are example information treatment decision screens of a graphical user interface (GUI) that can be presented to a physician, the figures respectively illustrating "do not discharge patient," "physician judgment," and "discharge patient" recommendations.
Figure 5B:
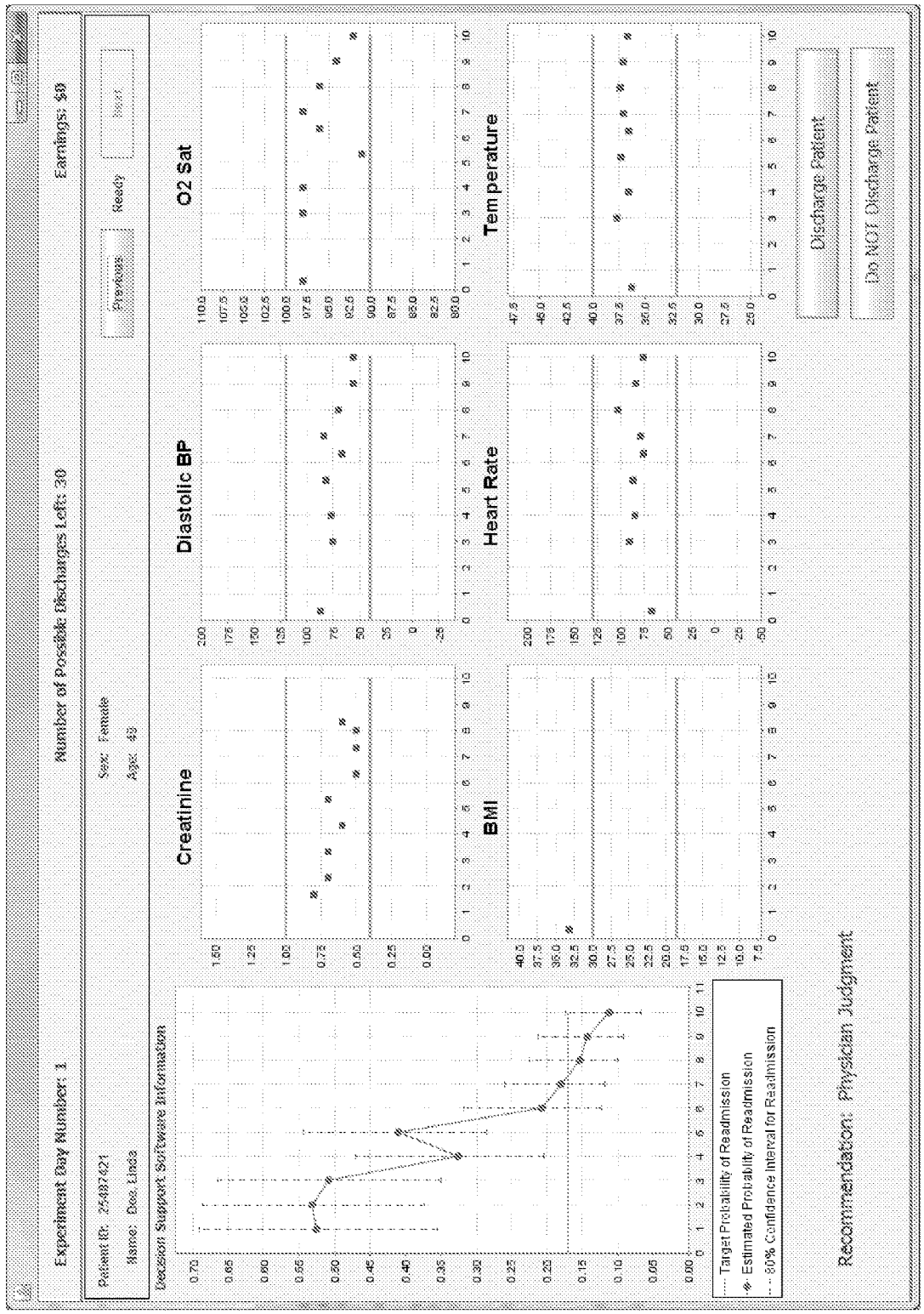
Figure 5C:
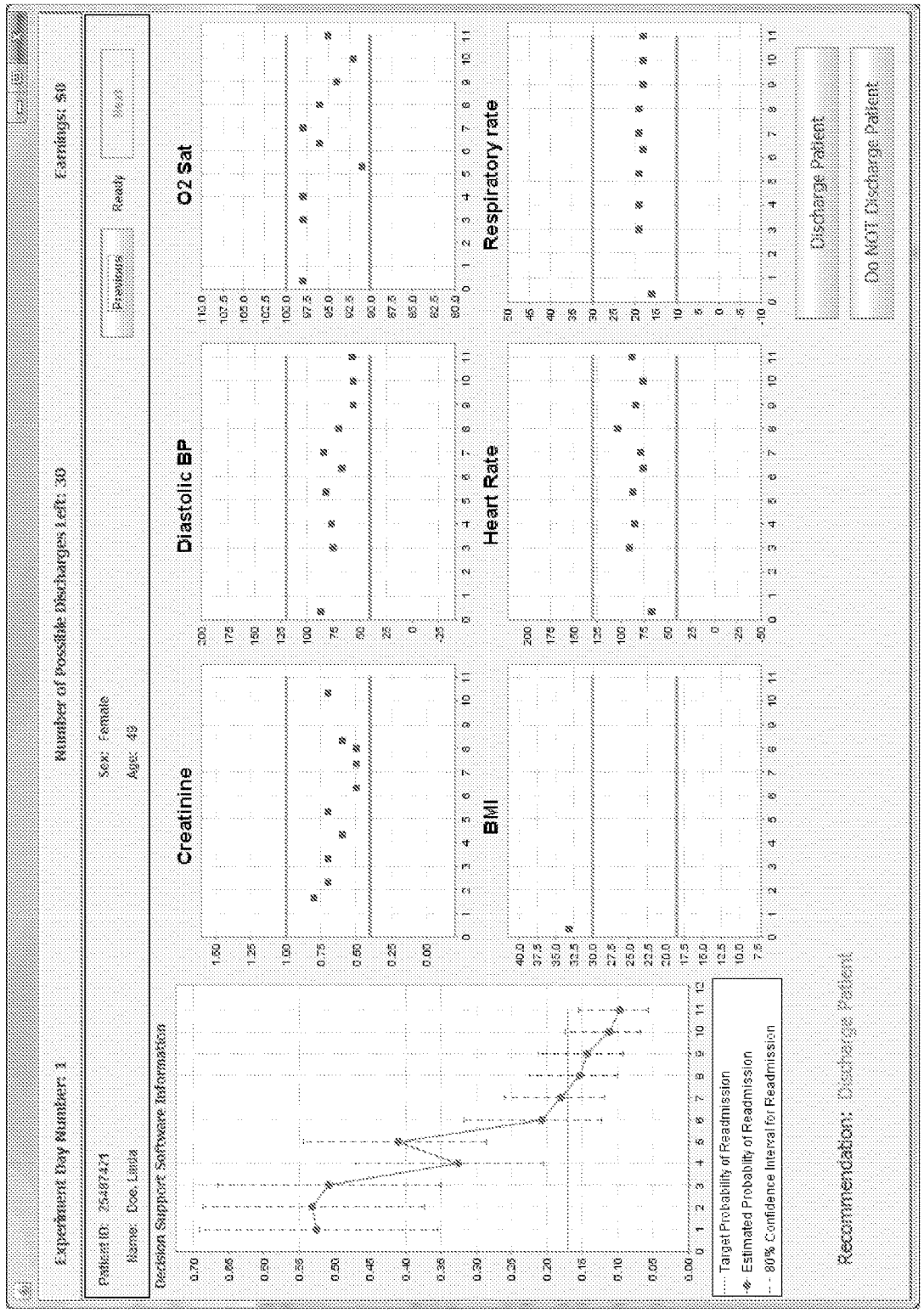

It is noted that, when the marginal effect for the various pieces of patient data is determined, the physician can also be provided with patient data that is most predictive of whether or not the patient will be readmitted. By way of example, graphs can be provided for each of several pieces of clinical data that plot the relevant values over the course of the various days of the hospital stay. FIGS. 5A-5C illustrate examples of this. In addition to including a graph that plots the probability estimates, confidence intervals, and target probability of readmission, graphs are provided for various clinical data that may further assist the physician in making a discharge decision. For example, in FIG. 5A, on the fifth day of a patient's hospital stay, graphs are provided for each of bilirubin, body mass index, heart rate, white blood cell count, diastolic blood pressure, and respiratory rate. These pieces of patient data have been presented because, as of that day, they are most statistically significant as to whether or not the patient will be readmitted in the predetermined time period. In FIG. 5B, however, on the tenth day of the patient's hospital stay, creatinine, diastolic blood pressure, oxygen saturation, body mass index, heart rate, and body temperature are the pieces of patient data that are presented to the physician for consideration. In FIG. 5C, on the eleventh day of the patient's hospital stay, creatinine, diastolic blood pressure, oxygen saturation, body mass index, heart rate, and respiratory rate are the pieces of patient data that are presented to the physician for consideration.

As can also be appreciated from FIGS. 5A-5C, the discharge recommendation changed over time. On day 5 (FIG. 5A), the probability estimate was above the target probability of readmission. Therefore, a "Do Not Discharge Patient" recommendation was provided. On day 10 (FIG. 5B), the target probability of readmission was between the probability estimate and upper end of the confidence interval. Therefore, a "Physician Judgment" recommendation was provided. On day 11 (FIG. 5C), the target probability of readmission was above the confidence interval. Therefore, a "Discharge Patient" recommendation was provided.

With reference back to FIG. 3, irrespective of the manner of the information that is presented to the physician, flow at this point depends upon whether or not the patient has been discharged (block 92). If not, flow returns to block 80, new patient data is collected for the patient under consideration and a new probability estimate is made for the next period (e.g., day). In this manner, the estimated probability is dynamically updated each period so as to be based on the most up-to-date information available as to the patient's current condition. Flow continues in this manner until the patient is discharged. As indicated in block 94, the patient under consideration's patient variables can be added to the discharge decision support model to update it with new data. In this manner, the model can evolve over time to reflect the ways in which readmission rates change over time.

A prototype discharge decision support model was constructed and tested for evaluation purposes. EMR data was obtained for 3,202 patients who underwent complex gastrointestinal surgery at a large southeastern hospital between the dates of January 2007 and December 2009, stayed in the hospital for at least three days, and had a complete clinical profile of medical history, vital sign reports, and laboratory test results during their hospital stay. Additional data was obtained from the EMR on the medications administered, any diagnostic imaging that was conducted, the patient's diet status, and whether or not blood transfusions were provided. The patient's home address was also linked to their census tract to retrieve additional census tract level information (e.g., housing value and education level). Once the information was abstracted from the clinical data warehouse, it was de-identified using the "safe harbor" method as defined by the HIPAA Privacy Rule Section 164.514(B)(2). The de-identified data was stored on a secure password-protected server. Clinical data was recorded in real time during the patient's stay in the hospital. Therefore, the date and time was obtained for each of the observations. As a first step in the analysis, a virtual patient chart was constructed for each patient that divided each day into eight-hour intervals. All of the variables were then assigned to one of the eight hour intervals based on the date and time that observation was recorded. In cases in which more than one observation was recorded in a particular time interval, the average value was assigned to the time interval. The virtual patient charts were used in the estimation of the discrete choice model and in the experimental software.

The primary outcome that was the focus of the discrete choice model was the probability of readmission within 30 days of being discharged from the hospital (the Medicare criterion). A probit regression model was the discrete choice model disclosed above and was used to estimate the probability of readmission. Since occurrence of the event of readmission is a binary variable, the information contained in a virtual patient chart on the day of discharge was used to estimate the probability of readmission (N=3,202). The variables constructed comprised the average values during a patient's stay, the duration of time spent in, out, and within the normal range of values expected for a particular observation, counts of medications, images and transfusions, as well as a full set of interaction terms between the laboratory test and vital sign variables.

Following construction of the data set, over 900 variables were obtained that could influence the probability of readmission. A fair number of these variables were highly correlated due to the biophysical nature of the data. To address the issue of multi-colinearity, some variables were eliminated when a linear correlation greater than 0.90 with other variable(s) was detected. The elimination of variables was hierarchically determined in consultation with physicians in order to ensure that the variables retained would provide the most reliable profile of patient status.

Following estimation, the patient chart data was used to construct a data set that contained the current value of each patient's relevant variables over the course of their stay. This resulted in a data set comprising 48,889 unique patient-day observations that corresponded to the observed value of each patient's data for each day during the hospital stay. This data set was then used to impute the predicted probability of readmission for the patient if they were discharged from the hospital on that day using the probit estimates from the estimation algorithm discussed earlier. In addition to predicted probabilities, 80% confidence intervals were constructed using the estimated parameter distributions. An 80% confidence interval was selected because it captures a 10% one-sided error on the decision criterion to discharge a patient on a given day.

An illustration of the estimated readmission probabilities is presented in FIG. 4 for a sample patient used in the experiment. The kinks in the solid piecewise linear graph show the point estimates of the readmission probabilities (vertical axis) if the patient were to be discharged on any one of several days during the hospital stay (horizontal axis). The dashed piecewise linear graphs show the upper and lower bounds on the 80% confidence interval for the readmission probabilities. The horizontal (solid) line shows the target readmission probability for all patients with the same diagnosis code as the patient in this chart. The predicted readmission probabilities and confidence intervals provide primary inputs for the experiment software.

In order to test the model, 30 patients were selected from the sample of 3,202 patients used in the regression model. To select the 30 patient charts, the 3,202 patients were partitioned into low, medium, and high readmission risk patients. The partitioning was based on the historically observed readmission rates for the procedures being conducted. A "low risk" patient had a procedure with a historically observed readmission rate less than 10%, a "medium risk" patient was between 10% and 20%, and a "high risk" patient was greater than 20%. These risks are not patient-specific but associated with the complexity of the surgery and the procedure-specific potential for infection and other complications. Based on this partition, 10 patient charts were selected from each of the three tiers to be used in the experiment. Patient charts that provided a clear test of the efficacy of the software were used by selecting patient charts for which the decision support software recommends (a) "do not discharge" on the first day and (b) "discharge" on some subsequent day in the chart. FIG. 4 provides an example of a chart with these properties.

The targeted readmission rates represent a uniform 10% reduction in readmission rates and are based on the 10% target stated by the Center for Medicare and Medicaid Services in 2010. The discharge decision support software used the estimated readmission probabilities and confidence intervals to make recommendations to a physician on a daily basis. In the case that the point estimate of the probability of readmission (piecewise linear graph in FIG. 4) is above the targeted readmission rate (horizontal line in FIG. 4) the software recommended that the patient not be discharged. If the point estimate lies below the target rate but the upper bound of the 80% confidence interval lies above the target readmission rate, the software makes a "physician judgment" recommendation; in essence, it makes no recommendation and leaves the decision up to the discretion of the physician (but provides additional information on the readmission probability and in six dynamically-selected clinical variable charts, as explained below). Lastly, if the upper bound of the 80% confidence interval lies below the targeted readmission rate the software recommends that the patient be discharged from the hospital.

Figure 6:
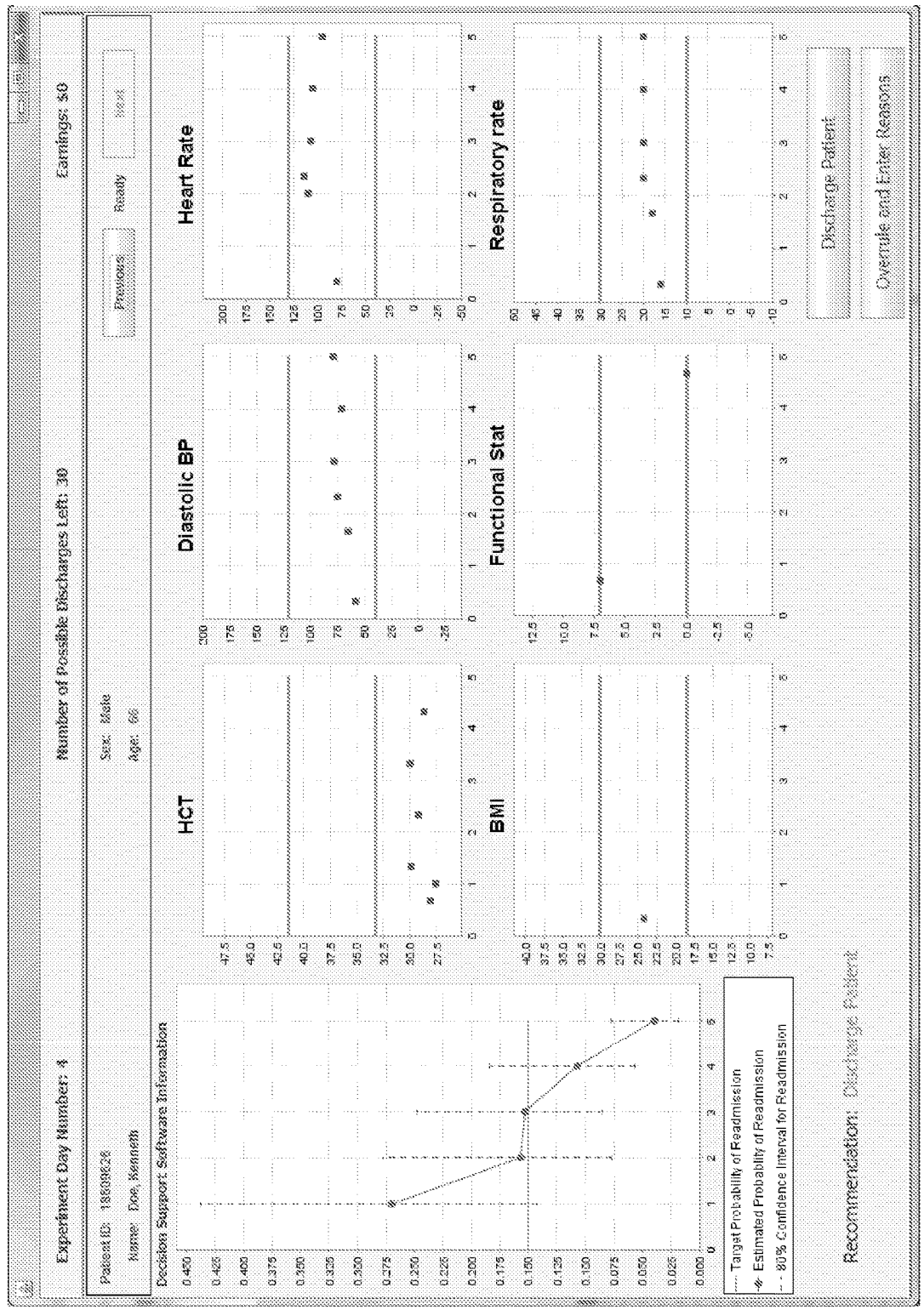
FIG. 6 is an example default treatment decision screen of the GUI that illustrates a positive discharge recommendation.

For the sample patient shown in FIG. 4, the decision support software's recommendations would be: (a) "do not discharge" on days 1-5; (b) "physician judgment" on days 6-10; and (c) "discharge" beginning on day 11. This patient was actually discharged on day 12. Of course, a physician will receive on day t only the recommendation for that day and the part of the time series of probabilities and clinical variables from day 1 through day t. Further examples are presented in FIGS. 5 and 6.

In addition to discharge recommendations and readmission probabilities, the software dynamically displayed six charts of selected patient data that the regression model indicates are significant for the health status of the patient on that day of the hospital stay. Ideally, one would like to estimate the marginal effect that each specific observation within the patient's virtual chart has on the readmission probability at a specific point in time. However, given the exceptionally large number of daily observations, such estimation may be computationally intractable for a software system that requires continuous daily updating. Therefore, a quasi-marginal effect of each variable was estimated by increasing the value of each type of laboratory test and vital sign variable observed for a patient by 1%, holding the other lab and vital data variables constant. This procedure yielded an estimated change in the daily probability of readmission if the variable should change slightly at that point in time. These quasi-marginal effects were then ordered according to their absolute values and used in selection of the six variables that possessed the highest quasi-marginal effects at that point in time. Given this construction, the clinical variables displayed in the six charts for a patient would change during the course of the experiment to reflect the information that was most relevant to the physician's decision at that point in time. The six activated panels contain a temporal plot of the patient data as well as upper and lower bounds on the normal range of values for each dynamically-selected clinical variable (as in FIGS. 5 and 6).

Figure 7:
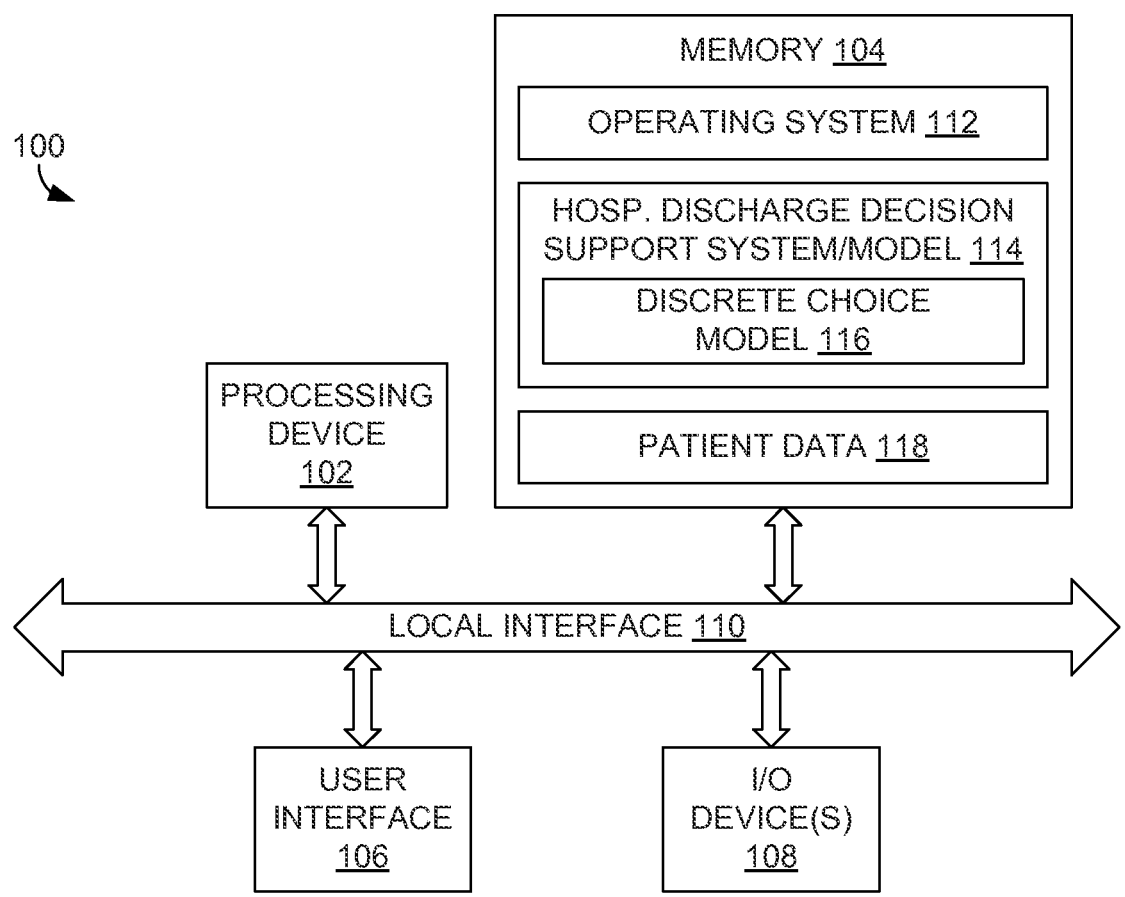
FIG. 7 is a block diagram of an embodiment of a computing device configured to assist a physician with a hospital discharge decision.

FIG. 7 is a block diagram of an example architecture for a computing device 100 that can be used to execute software configured to assist a physician with a discharge decision. As is shown in FIG. 7, the computing device 100 generally comprises a processing device 102, memory 104, a user interface 106, and one or more input/output devices 108, each of which is connected to a system bus 110.

The processing device 102 can comprise a central computing processor (CPU) that is capable of executing instructions stored within the memory 104. The memory 104 is a non-transitory computer-readable medium that can include any one or a combination of volatile memory elements (e.g., a random access memory (RAM)) and nonvolatile memory elements (e.g., hard disk, flash memory, etc.). The user interface 106 comprises the components with which a user (e.g., physician) interacts with the computing device 100, such as a keyboard, mouse, and display. The I/O devices comprise the components adapted to facilitate communication with other devices.

Stored within memory 104 are various programs that include algorithms (logic), including an operating system 112 and a hospital discharge decision support system or model 114. The operating system 112 governs general operation of the computing device 100 while the hospital discharge decision support system/model 114 is configured to assist physicians with discharge decisions using the methods described in the foregoing disclosure. As indicated in FIG. 7, the system/model 114 can comprise a discrete choice model that is configured to estimate the mathematical probability of a patient being readmitted to a hospital after being discharged. As is further shown in FIG. 7, the memory 104 can store patient data 118, which can include the real-time data continually collected for one or more patients who are staying at a hospital.

The invention claimed is:

1. A method for assisting a physician with a hospital discharge decision, the method comprising, on each day of a hospital stay of a patient under consideration:
collecting patient data from the patient under consideration and using the patient data to construct patient variables that are indicative of a likelihood of the patient under consideration being readmitted if released from the hospital on that day;
estimating using a discrete choice model a mathematical probability of the patient under consideration being readmitted to the hospital within a predetermined amount of time if the patient under consideration were discharged on that day, wherein the discrete choice model has been trained using historical patient data of former hospital patients who have been admitted to and later released from a hospital, the training comprising using the historical patient data to create historical patient variables and selecting the historical patient variables that are most statistically significant in predicting hospital readmittance using an iterative process in which the least statistically significant historical patient variables are removed from the discrete choice model, wherein the mathematical probability estimate is based upon a comparison of the constructed patient variables and the historical patient variables; and
presenting to the physician a graph that plots the estimated mathematical probabilities as a function of day of the week, the graph including calculated confidence intervals for the estimated mathematical probabilities and a target probability, wherein discharge is not recommended on any day that the estimated mathematical probability is above the target probability but is recommended on any day that the confidence interval is below the target probability.

2. The method of claim 1, wherein the collecting patient data comprises collecting at least one of diet data, imaging data, lab data, medicine data, nurse data, patient-specific data, transfusion data, and vital data.

3. The method of claim 2, wherein the patient-specific data includes demographic information about the patient under evaluation.

4. The method of claim 1, wherein constructing patient variables comprises normalizing the patient data.

5. The method of claim 4, wherein the patient variables include at least one variable that comprises an interaction of two different pieces of patient data.

6. The method of claim 4, wherein the patient variables include at least one time-constructed variable that correlates patient data with the time it was collected.

7. The method of claim 1, wherein the discrete choice model is one of a probit model, a logit model, a support vector machine (SVM) with alternative kernel specifications, a neural network model with one or more hidden layers, a Bayesian Markov chain Monte Carlo (MCMC) model, a method of moments model, a simulated method of moments model, an expectation maximization (EM) algorithm, and a linear probability model.

8. The method of claim 1, wherein the discrete choice model applies parameter estimates to the patient variables that take into account the relative statistical significance of the patient variables in predicting whether or not the patient under consideration will be readmitted.

9. The method of claim 1, further comprising determining which pieces of collected patient data are most predictive of whether or not the patient under consideration will be readmitted if discharged on that day and presenting that collected patient data to the physician along with the graph of estimated mathematical probabilities.

10. A non-transitory computer-readable medium that stores a system for assisting a physician with a hospital discharge decision on each day of a hospital stay of a patient under consideration, the system comprising:
logic configured to receive patient data collected from the patient under consideration;
logic configured to construct patient variables from the patient data that are indicative of a likelihood of the patient under consideration being readmitted if released from the hospital on that day;
a discrete choice model configured to estimate a mathematical probability of a patient under consideration being readmitted to a hospital within a predetermined amount of time if the patient under consideration were discharged on that day, wherein the discrete choice model has been trained using historical patient data of former hospital patients who have been admitted to and later released from a hospital, the training comprising using the historical patient data to create historical patient variables and selecting the historical patient variables that are most statistically significant in predicting hospital readmittance using an iterative process in which the least statistically significant historical patient variables are removed from the discrete choice model, wherein the mathematical probability is based upon a comparison of the constructed patient variables and the historical patient variables; and
logic configured to present to the physician a graph that plots the estimated mathematical probabilities as a function of day of the week, the graph including calculated confidence intervals for the estimated mathematical probabilities and a target probability, wherein discharge is not recommended on any day that the estimated mathematical probability is above the target probability but is recommended on any day that the confidence interval is below the target probability.

11. The computer-readable medium of claim 10, wherein the discrete choice model is configured to construct the patient variables by normalizing the patient data.

12. The computer-readable medium of claim 10, wherein the discrete choice model is one of a probit model, a logit model, a support vector machine (SVM) with alternative kernel specifications, a neural network model with one or more hidden layers, a Bayesian Markov chain Monte Carlo (MCMC) model, a method of moments model, a simulated method of moments model, an expectation maximization (EM) algorithm, and a linear probability model.

13. The computer-readable medium of claim 10, wherein the discrete choice model applies parameter estimates to the patient variables that take into account the relative statistical significance of the patient variables in predicting whether or not the patient under consideration will be readmitted.

14. The computer-readable medium of claim 10, wherein the discrete choice model is further configured to determine the collected patient data that is most predictive of whether or not the patient under consideration will be readmitted if discharged on that day and to present that collected patient data to the physician along with the graph of estimated mathematical probabilities.

15. A method for constructing a hospital discharge decision support model, the method comprising:
   accessing historical patient data of a population of former hospital patients whose readmission outcomes are known; and
   constructing a discrete choice model configured to calculate a mathematical probability of a patient under consideration being readmitted to the hospital within a predetermined amount of time if the patient under consideration were discharged on the present day, wherein constructing the discrete choice model comprises training the discrete choice using the historical patient data to create historical patient variables, and identifying the historical patient variables that are most statistically significant in predicting hospital readmittance using an iterative process in which the least statistically significant historical patient variables in view of the known readmission outcomes are removed from the discrete choice model;
   wherein the discrete choice model is configured to calculate the mathematical probability based upon a comparison of the historical patient variables with like patient variables constructed based upon patient data collected from the patient under consideration on the present day.

16. The method of claim 15, wherein constructing a discrete choice model further comprises filtering the historical patient data to remove outlier data before constructing the set of historical patient variables.

17. The method of claim 16, wherein constructing a discrete choice model further comprises normalizing the filtered historical patient data before constructing the set of historical patient variables.

18. The method of claim 17, wherein constructing a discrete choice model further comprises eliminating collinear historical patient variables.

19. The method of claim 15, wherein constructing a discrete choice model further comprises determining the statistical significance of each historical patient variable in predicting readmission and iteratively eliminating the least statistically significant historical patient variables.

20. The method of claim 15, wherein the discrete choice model is one of a probit model, a logit model, a support vector machine (SVM) with alternative kernel specifications, a neural network model with one or more hidden layers, a Bayesian Markov chain Monte Carlo (MCMC) model, a method of moments model, a simulated method of moments model, an expectation maximization (EM) algorithm, and a linear probability model.

* * * * *